(12) United States Patent
Yeganeh et al.

(10) Patent No.: US 7,553,449 B2
(45) Date of Patent: Jun. 30, 2009

(54) METHOD OF DETERMINATION OF CORROSION RATE

(75) Inventors: Mohsen S. Yeganeh, Piscataway, NJ (US); Shawn M. Dougal, Livingston, NJ (US); Cheayao Zhang, Annandale, NJ (US); Saul C. Blum, Monroe, NJ (US); H. Alan Wolf, Franklin Lakes, NJ (US); Glen Barry Brons, Phillipsburg, NJ (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 656 days.

(21) Appl. No.: 10/946,049

(22) Filed: Sep. 21, 2004

(65) Prior Publication Data

US 2006/0063263 A1    Mar. 23, 2006

(51) Int. Cl.
*G01N 17/00* (2006.01)
(52) U.S. Cl. .................. 422/53; 436/6; 356/237.2; 250/341.1; 250/301; 73/104
(58) Field of Classification Search .............. 422/53; 436/60, 6; 356/237.2; 250/301, 341.1; 73/104
See application file for complete search history.

(56) References Cited

U.S. PATENT DOCUMENTS

| | | | |
|---|---|---|---|
| 4,469,442 A * | 9/1984 | Reich | 356/364 |
| 4,748,329 A * | 5/1988 | Cielo et al. | 250/559.28 |
| 5,155,555 A | 10/1992 | Wetegrove et al. | 356/381 |
| 5,332,900 A | 7/1994 | Witzke et al. | 250/341 |
| 5,411,890 A * | 5/1995 | Falat | 436/6 |
| 5,793,042 A * | 8/1998 | Quick | 250/339.08 |
| 5,804,140 A | 9/1998 | Kishi et al. | 422/53 |
| 6,151,116 A * | 11/2000 | Hirosawa | 356/369 |
| 7,057,177 B2 * | 6/2006 | Davis et al. | 250/341.8 |
| 7,274,443 B2 * | 9/2007 | Ponstingl et al. | 356/237.2 |

FOREIGN PATENT DOCUMENTS

DE    19931128 A1 *    1/2001

* cited by examiner

*Primary Examiner*—Lyle A Alexander
*Assistant Examiner*—Dennis M White
(74) *Attorney, Agent, or Firm*—Glenn T Barrett

(57) ABSTRACT

The corrosion rate of a metal immersed in a fluid medium is measured by transmission of a beam of radiation normally in the visible or near infra-red portion of the spectrum, through a thin film of the metal immersed in the medium. The film of the metal is suitably supported on a radiation-transmitting substrate such as a glass plate or slide. The corrosion rate can be determined by passing a radiation beam through the metal film sample using a twin beam system to compensate for instrument factors such as the absorbance by the fluid medium, the cell windows and the film-supporting substrate. As the thickness of the film decreases, the reduction in film thickness is determined by the increase in beam intensity, using a reference beam to compensate for the instrument factors.

7 Claims, 3 Drawing Sheets

METHOD OF DETERMINATION OF CORROSION RATE

FIELD OF THE INVENTION

This invention relates to a method of determining the corrosion rate of a material exposed to a corrosive environment. It is particularly applicable to the determination of the rate of corrosion of metals in the presence of corrosive gases and liquid streams, for example, those encountered in a petroleum refinery.

BACKGROUND OF THE INVENTION

The corrosion of metal equipment by petroleum products is a continuing problem in the design, construction and operation of refining equipment. Two principal corrosion mechanisms that can occur in petroleum streams: metal dissolution, for example, by naphthenic acid attack and/or scale formation, for example, sulfide scale formation from reactive sulfur attack. The extent of corrosion which is encountered in actual practice may be controlled by limiting the corrosivity of the product or by the appropriate choice of material for the equipment. In practice, either the level of certain impurities is specified or the degree of corrosion of a specific metal which is allowable under standardized test conditions is specified. In either event, it is necessary to determine the susceptibility of a metal to corrosion under the expected conditions of use. A number of methods have evolved to this end. The copper strip corrosion tests approved by the ASTM such as ASTM D 130 and D 1838-84 are examples. Copper is chosen in these tests because it is the most corrosion sensitive metal encountered by most petroleum products. In many cases sulfur containing species such as hydrogen sulfide, mercaptans, organic sulfides, carbonyl sulfide and even elemental sulfur are the corrosive agents of prime concern in petroleum refinery streams.

The Copper Strip Corrosion Test for LPG Gases (ASTM D 1838) together with similar methods, is a traditional type test, in which a metal token is exposed to the corrosive environment under specified conditions for a given period of time after which the token is inspected visually for any tarnish and compared to a standard color chart available from the ASTM to make a determination of the corrosivity of the selected environment. The test is clearly laborious, time consuming, imprecise and dependent upon the visual judgment of a human operator. Because of these shortcomings, various instrumented test techniques have evolved. U.S. Pat. No. 5,332,900 (Witzke), for example, describes a method for determining corrosion of a metal test token in a corrosive petroleum stream using a reflected light technique to assign an appropriate Copper Strip Test grade and to alert refinery operators to major contaminants in the product streams. Relying as it does, however, on the formation of a corrosion film, the method still requires a period of time for the film to develop, typically a quarter hour or longer, so that prompt determination of corrosion is not possible.

U.S. Pat. No. 5,804,140 (Kishi) describes a method of determining corrosion on metal test tokens using various film thickness measurement techniques including secondary ion mass spectrometer (SIMS) and x-ray microanalyzer (XMA). Whatever the method of measurement, however, the method also requires the corrosion film on the metal to grow for a predetermined period of time before its thickness can be measured, a factor limiting the speed with which corrosion can be determined.

U.S. Pat. No. 5,155,555 (Wetegrove) describes a method for monitoring film formation on the surface of a rotating test coupon immersed in the corrosive stream. This method, however, is even less amenable to real time operation because it requires the test coupon to be removed from the stream and the thickness measured outside the test chamber by a reflected light technique.

SUMMARY OF THE INVENTION

We have now devised a method and an instrument, which is capable of making rapid measurements of superficial corrosion; as will appear below, corrosion rates may be determined in a matter of seconds.

According to the present invention, the corrosion rate of a metal immersed in a fluid medium is measured by transmission through a thin film of the metal immersed in the medium. The corrosion rate can be determined by passing a beam of electromagnetic radiation through the metal film sample using a twin beam system to compensate for instrument factors such as the absorbance by the fluid medium, the cell windows and the film-supporting substrate. The metal film sample is illuminated with the radiation beam, preferably a light beam from a laser source or a beam of infra-red radiation, while the film is exposed to the stream being investigated. As the thickness of the film decreases, the reduction in film thickness is determined by the increase in intensity of the beam traversing the metal film, using the reference beam to compensate for the instrument factors.

In practical form, the method is carried out by passing a beam of radiation through a radiation-transmitting film of the metal immersed in the fluid medium in a test cell to determine the change in transmission through the metal film over a period of time during which it is immersed in the fluid; from this, the corrosion rate is determined from the change in transmission through the metal in this period of time. In the twin-beam compensation technique, the first beam traverses the metal film supported on a substrate which is transparent to the radiation being used and a reference beam traverses the same functional path through the test cell, that is, the same path except for the test film being investigated. The relative intensities of the emergent first and reference beams after passing through the test cell are then measured to determine the decrease in intensity resulting from passage through the metal film. Since the metal film has to be thin enough to be capable of transmitting the radiation, it is necessarily thin, typically, less than 100 nm in thickness. To provide support, the film is deposited on a radiation -transmitting substrate such as glass (for use in the visible spectrum) or fluorite (for use with infra-red) and the substrate is included in the functional light path traversed by the reference beam in the test cell.

The film thickness can be measured at defined intervals in order to determine the rate of corrosion of the metal/stream system. We have found that the initial corrosion rate which is normally marked by a marked decrease in film thickness is representative of the long-term corrosion rate that may be expected in the long-term operation of the same metal/stream system.

DRAWINGS

DETAILED DESCRIPTION

Figure 1:
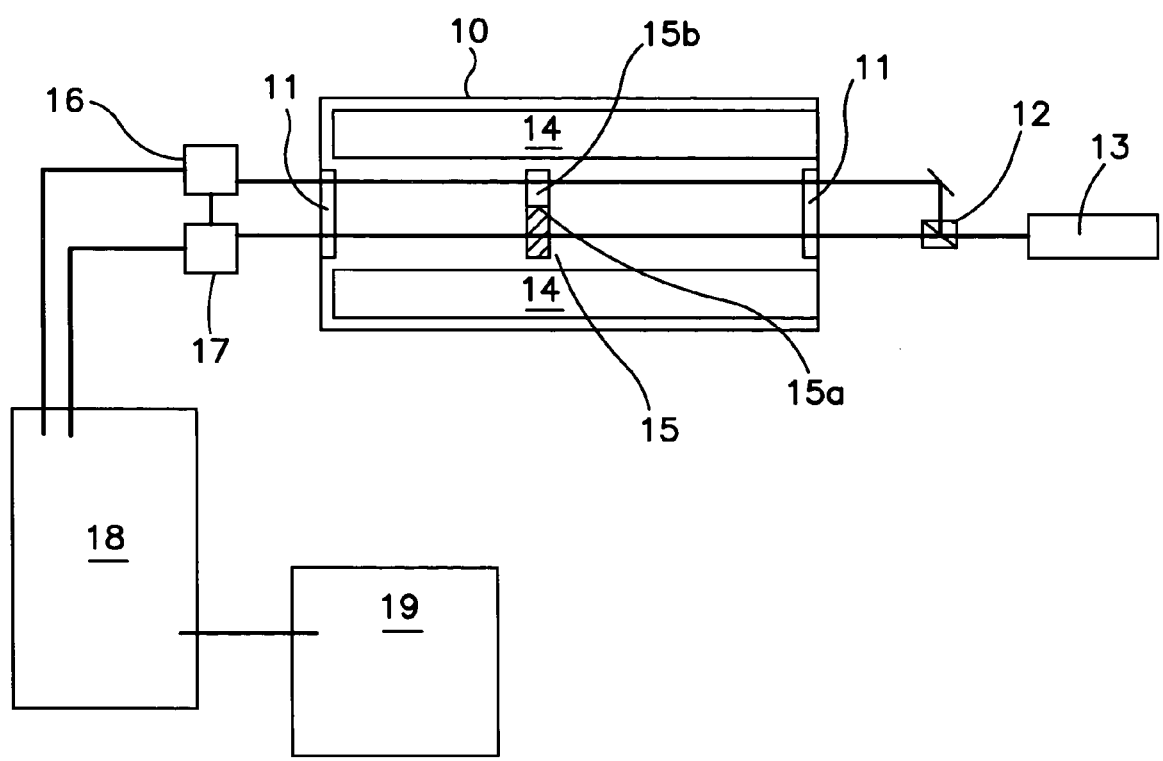
FIG. 1 shows schematically a typical arrangement for the test device.

A schematic of a suitable, exemplary form of the apparatus which may be used to operate the method is shown in FIG. 1.

A sample cell 10, suitably made of stainless steel, e.g. 316 stainless steel, has a clear glass window 11 at each end. A source of light at a wavelength in the visible portion of the spectrum, suitably a HeNe laser 13 producing light at 632.8 nm, provides a collimated beam which is split into two by beam splitter 12 before entering the corrosion cell through window 11. During the test, the cell is filled with the petroleum stream under investigation. The cell can be heated from ambient to the desired test temperature, typically up to 400° C., using an electrical heater coil 14 around the cell. The sample coupon 15 is in the form of a glass disk which is half coated with the selected material for the test (e.g. iron). Any suitable deposition method which is capable of depositing an appropriately thin layer of metal on the glass disk may be used. Sputtering and vacuum deposition, both of which are well established for this purpose may be used. Normally, the thickness of the metal film will be less than 100 nm so that the light can penetrate through the metal film. The thickness may vary for different metals.

One laser beam (sample beam) passes through the coated part 15a of the sample coupon and the other beam (reference beam) passes through the un-coated part 15b of the glass disk. The intensities of these beams are measured with two photodiode detectors 16, 17 outside the cell. The reference beam detected by detector 16 carries information about the change in environment (darkening of liquid, variation of intensity with temperature and other parameters that are intrinsic to the cell) encountered by the beam as it passes through the cell. The sample beam carries information about the environment as well as the thickness of the film. As the film becomes thinner due to corrosion processes, the intensity of the sample beam with respect to the reference beam becomes greater. The outputs from the photodiodes are then fed to suitable circuitry which may be either special purpose or, with an appropriate interface, a general-purpose computer with proper programming to interpret the outputs from the diodes. Special purpose circuitry might comprise a comparator and output system. The figure shows and analog-to-digital converter 18 which is connected to computer 19 to provide the desired indication of film thickness.

The corrosion rate can be determined from the intensities of the sample and reference beams as follows:

For the detected intensities:

$$I_s = I_{s0} f(\text{environment}) e^{-\frac{4\pi}{\lambda} Kd} \quad (1)$$

$$I_r = I_{r0} f(\text{environment})$$

where: $I_r$ is the intensity detected by the reference detector (light passing through the un-coated part of the disk), $I_s$ is the intensity detected by the sample detector (light passing through the coated part of the disk), $I_{s0}$ and $I_{r0}$ are the intensity of light before entering the cell and reaching the coated and un-coated part of the disk, respectively (these two parameters are measured at the beginning of the experiment and the ratio determined so that it becomes a constant), f(environment) describes all environmental parameters that change the signal intensity, d is the thickness of the film, L is the wave length of electromagnetic radiation and K is the extinction coefficient of the coated film.

From the above equations one obtains:

$$\frac{I_s}{I_r} = \frac{I_{s0}}{I_{r0}} e^{-\frac{4\pi}{\lambda} Kd} \quad (2)$$

or $$d = \frac{-\lambda}{4\pi K} \text{Ln}\left[\frac{I_s I_{r0}}{I_r I_{s0}}\right] \quad (3)$$

Since the variations of $I_s$ and $I_r$ with time are known from the measurements of light intensity, and $I_{r0}/I_{s0}$ is a constant fixed at the beginning of the measurement, the above equation describes the variation of the thickness with time as a function of the emergent light beam ratio. The derivative of d with respect to time will then provide the corrosion rate. If the corrosion rate varies linearly with time, as shown in Example 1, the slope of the plot of d, thickness, as a function of time is the corrosion rate.

It is observed that there is a marked decrease in the thickness of the coated metal film. This is the result of removal of metal by the corrosive action of the agent or agents in the test stream For the purposes of determining the rate of corrosion the slope of the thickness/time curve during the initial phase when the sharp decrease in film thickness takes place should be employed; it has been found that this determination will accord well with corrosion rates determined by other methods.

The metal chosen for the test will, of course, accord with the metal whose corrosion rate is under investigation. Often this will be a ferrous material such as carbon steel or stainless steel when corrosion rates for process equipment are being measured but the method may be extended to other metals, for example, to copper alloys, silver alloys or tin alloys if measurements of bearing corrosion rates are to be determined. The present method is very suitable, in fact, for measuring bearing corrosion rates since it provides a highly sensitive and rapid determination of very small amounts of metal removal. For the same reason, the method commends itself for use in determining the corrosion rates associated with additives such as, for example, antioxidants or detergents in petroleum fuels and lubricating oils. The fluids which are investigated by this technique may be either gaseous or liquid, for example, natural gas, liquid fuels such as gasoline, diesel, jet fuel, fuel oil, oils such as lubricating oils or industrial oils and functional fluids such as hydraulic fluids.

The electromagnetic radiation used to detect the variations in the film thickness may be selected mainly according to the absorption of radiation of a selected wavelength by the metal under investigation as well as by the absorption of the fluid and finally, by factors of convenience. Many fluids are reasonably transparent to radiation in the visible portion of the spectrum. For most purposes, light in the visible red portion of the spectrum, such as the coherent light at 632.8 nm produced by the HeNe laser mentioned above, will be suitable for many metals normally used in refinery equipment, especially ferrous metal alloys. Other portions of the visible spectrum may also be used, for example, the visible green at 532 nm from a laser source. Certain fluids, such as crude oil, absorb highly in the visible region of the spectrum, but have reasonable transmission in regions of the infrared. An infrared light source such as infrared diode laser or any other light source producing radiation in the regions of transmission may be employed. Although the use of coherent radiation is preferred it is not essential: incandescent filament or other sources may be used although laser sources including laser diodes will often be most convenient.

The light-transmitting substrate upon which the metal film is deposited is normally glass for radiation in the visible portion of the spectrum but other media which can be produced with satisfactory clarity and uniformity may also be used. When operating with infra-red, fluorite should be used. Because the twin-beam compensation relies on the uniformity of the test coupon substrate, care should be taken in the selection of the coupons to ensure that proper compensation will be achieved. Normally, this will be no problem with well-manufactured coupon substrates. Cell windows should be chosen in the light of the same factors.

The rapid determination which is afforded by the method enables it to be used in high throughput experimentation for the rapid screening of refinery streams for corrosivity as well as for making rapid determinations of the effectiveness of corrosion inhibitors dissolved in these streams.

EXAMPLE 1

A glass disk was half coated with iron using a sputtering technique. The iron-coated glass was then exposed to air for oxidation. The surface of the sample was cleaned prior to the measurement using a plasma chamber. The value of $I_{r0}/I_{s0}$ was measured to be 0.480, using a He/Ne laser of 5 mW output with a monochromatic wavelength of 632.8 nm. Process oil (25 grams of Tufflo™) containing 248 mg of TCI naphthenic acid, (corresponding to TAN=2) was preheated to 270° C. before the coated glass (sample) was added to the cell. The temperature of the cell was raised to 300° C. and the collection of data began. The cell was under a nitrogen blanket during the measurement.

Figure 2:
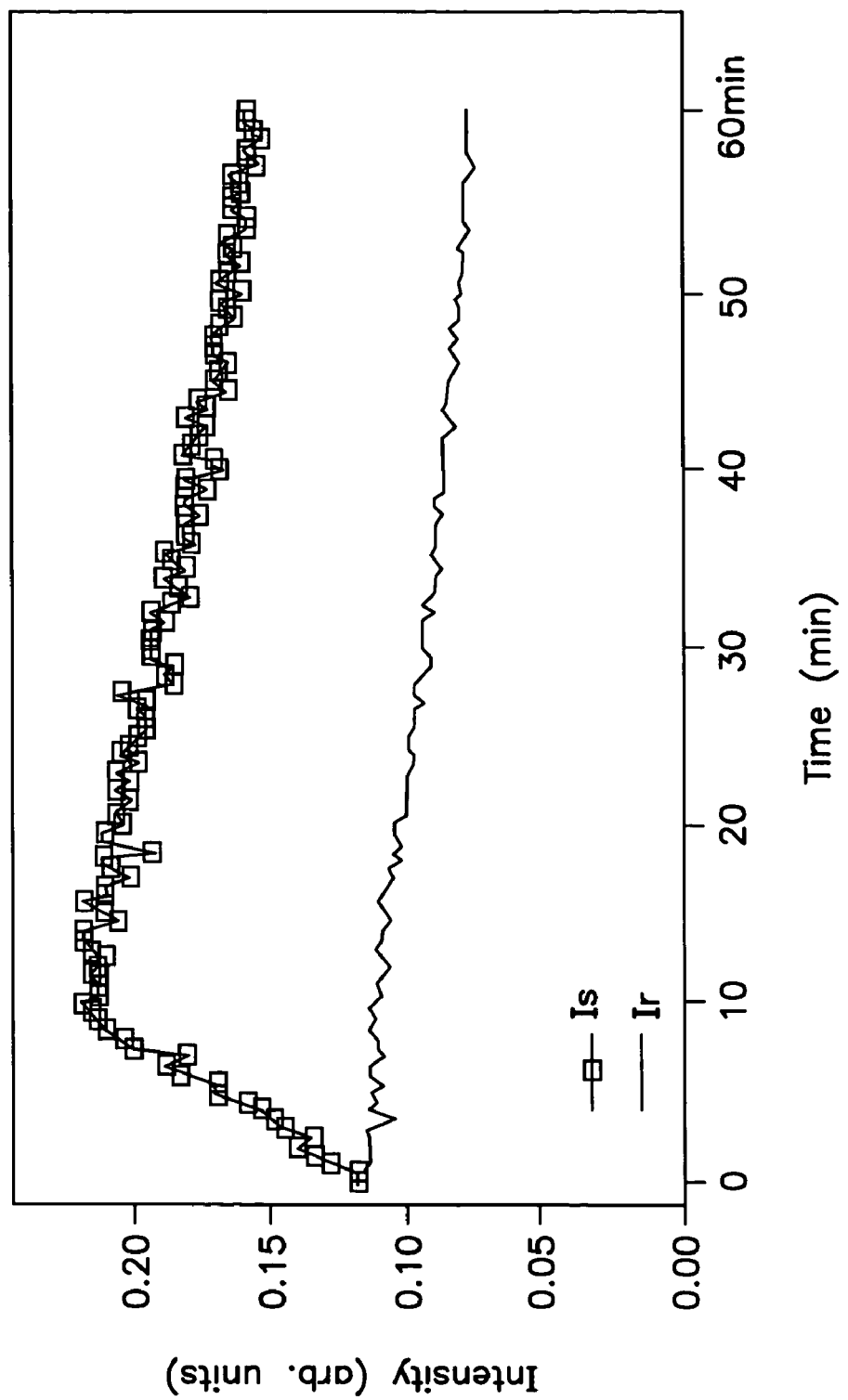
FIG. 2 shows the time variant intensity of a light beam transmitted through the test coupon.

FIG. 2 shows a plot of $I_s$ and $I_r$ as a function of time. The variation of $I_r$ with respect to time describes the effect of all possible environmental parameters that could change the intensity of the laser beam passing through the system. The variation of $I_s$ with time carries information similar to $I_r$, plus the effect of the film thickness. As shown in the figure, the $I_s$ intensity increases with time and then follows the $I_r$ variation. The initial increase is mainly due to the thinning of the film, resulting from the corrosion of the iron oxide film.

Figure 3:
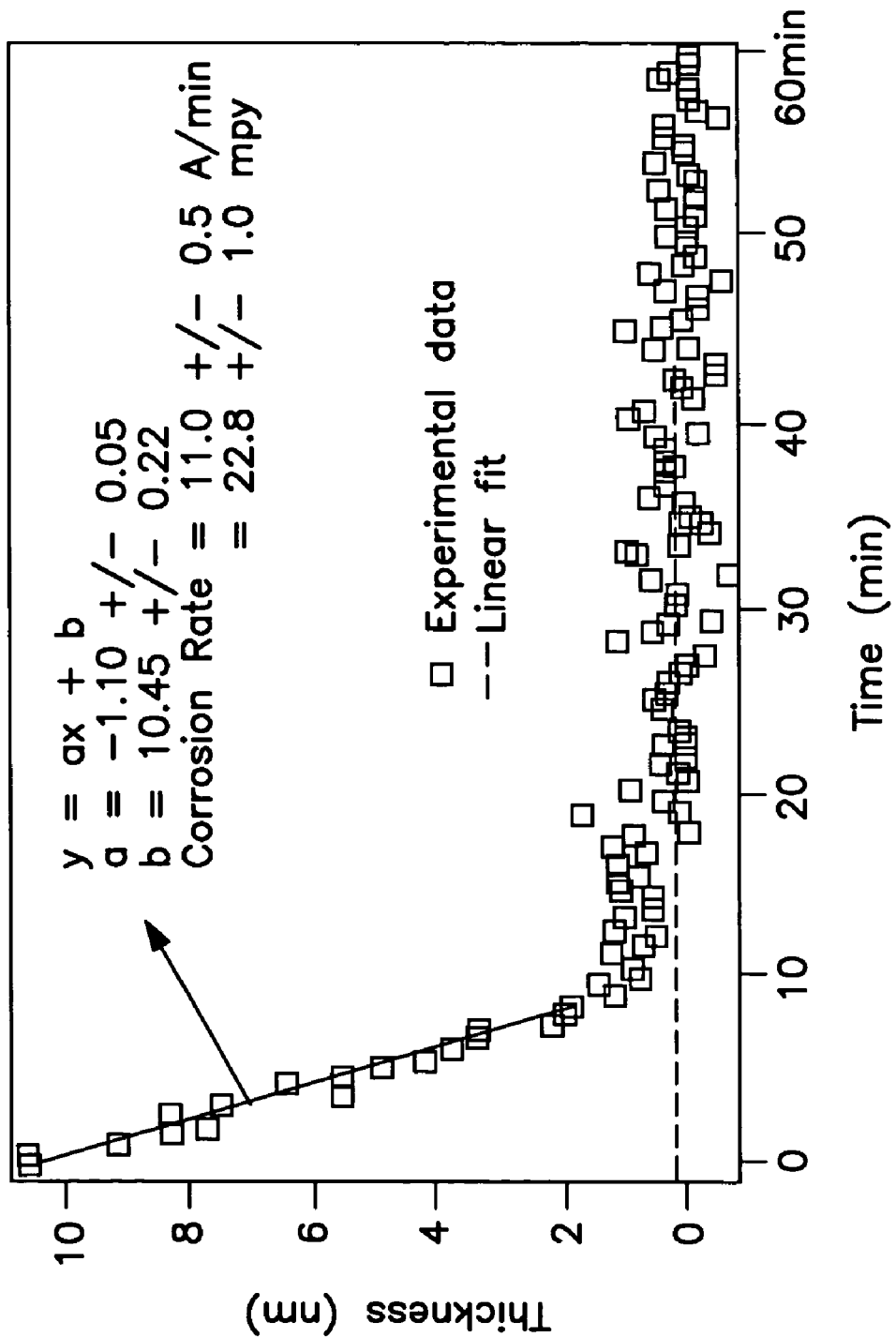
FIG. 3 shows the time variant thickness of the test coupon.

In FIG. 3 the variation of thickness, d, with time is shown using Eq. (3). For this calculation the thickness, k, the extinction coefficient of iron, is taken to be 3.364 at the wavelength of 632.8 nm used. This value of k is extrapolated from values given in the CRC Handbook.

FIG. 3 shows the thinning of the film with time for the first 10 minutes. This variation is linear and the slope of the line represents the corrosion rate of $1.10+/-0.05$ nm. $\min^{-1}$. This value is equivalent to 22.8+/-1.0 mils per year.

EXAMPLE 2

In this example the corrosion rate of an oil with a Total Acid Number (ASTM D-664) of 2 was determined using a lost mass measurement. This example was carried out for comparison.

The details of the apparatus used in this example are given in U.S. patent application Ser. No. 10/675,530 (Publn. No. 20040107769A1, corresponding to WO 2004/044094). Briefly, the reaction apparatus consists of a 250 ml round-bottom flask equipped with a thermocouple, heater, reflux, with sample holder and system. 110 g of Tufflo™ process oil was put in the flask and its temperature brought to 300° C. A carbon steel coupon with dimensions of approximately 20×12×3 mm and weight of 6.7373 g was immersed into the oil and 0.84 grams of naphthenic acid was added to the oil, giving a total acid number of 2 mg KOH/g. The coupon was kept in the solution for 6 hours and was then rinsed with solvent and gently dried with lint free paper. The coupon's weight was 6.7343 g after this procedure, corresponding to a mass loss of 3 mg and a corrosion rate of 27 mils per year.

The result obtained from the current method is in excellent agreement with the results obtained from traditional mass loss measurements. However, the current method achieves produces this result significantly faster than the traditional method.

The invention claimed is:

1. A method of determining the corrosion rate of a sample of a metal immersed in a fluid medium, comprising
    providing a sample coupon having a first portion and a second portion, wherein a light-transmitting film of the sample of the metal being applied to the first portion of the sample coupon, wherein the second portion of the sample coupon is uncoated;
    immersing the sample coupon in the fluid medium in a test cell;
    passing a first beam of radiation through the first portion of the sample coupon having the light-transmitting film of the metal thereon, whereby the first beam travels through the first portion of the sample coupon having the light-transmitting film of the metal thereon;
    determining the change in transmission of the radiation through the metal over a period of time during which it is immersed in the fluid medium, wherein determining the change in transmission includes passing a second beam of radiation through the second uncoated portion of the sample coupon, wherein the second beam traversing substantially the same functional path as the first beam such that the second beam travels through the second uncoated portion of the sample coupon, and comparing the relative intensities of the first beam and the second beam after the first beam and the second beam pass through the test cell; and
    determining the corrosion rate from the change in transmission through the metal in the period of time.

2. A method according to claim 1, wherein the relative intensities of the first and second beams after the beams pass through the test cell are correlated to the relative intensities of the first and second beams before passing through the test cell.

3. A method according to claim 1, wherein the sample coupon is a radiation-transmitting substrate.

4. A method according to claim 1, wherein the first and second beams of radiation are light in the visible portion of the electromagnetic spectrum.

5. A method according to claim 1, wherein the first and second beams of radiation are infra-red radiation in the near infra-red portion of the electromagnetic spectrum.

6. A method according to claim 4, wherein the sample coupon comprises glass.

7. A method according to claim 5, wherein the sample coupon comprises fluorite.

* * * * *